Figure 1:
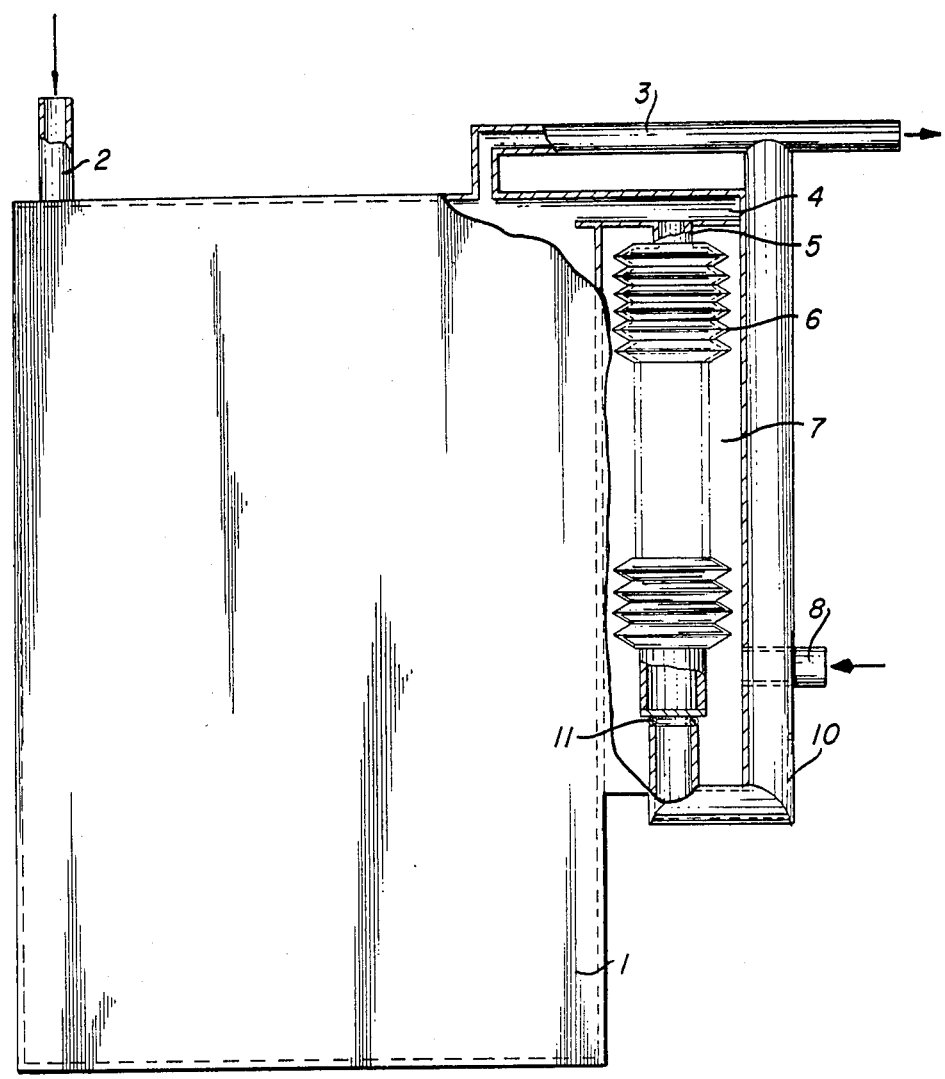

United States Patent [19]

Kurtz et al.

[11] Patent Number: 4,718,895
[45] Date of Patent: Jan. 12, 1988

[54] SUCTION REGULATOR

[75] Inventors: Robert J. Kurtz, New York; Joseph LiCausi, Port Jefferson Station, both of N.Y.

[73] Assignee: Bioresearch Inc., Farmingdale, N.Y.

[21] Appl. No.: 780

[22] Filed: Jan. 6, 1987

Related U.S. Application Data

[63] Continuation-in-part of Ser. No. 821,530, Jan. 24, 1986, abandoned, which is a continuation-in-part of Ser. No. 667,814, Nov. 2, 1986, abandoned.

[51] Int. Cl.$^4$ .............................................. A61M 1/04
[52] U.S. Cl. .................................. 604/119; 604/319; 137/205; 137/510; 137/907
[58] Field of Search ............... 137/205, 510, 907, 908, 137/614.2; 604/119, 319, 320, 321

[56] References Cited

U.S. PATENT DOCUMENTS

| | | | |
|---|---|---|---|
| 3,189,042 | 6/1965 | Kerley | 137/493.9 |
| 3,363,626 | 1/1968 | Bidwell | 128/276 |
| 3,599,639 | 8/1971 | Spotz | 128/276 |
| 3,624,821 | 11/1971 | Henderson | 417/137 |
| 4,396,386 | 8/1983 | Kurtz et al. | 604/319 |
| 4,468,226 | 8/1984 | Kurtz et al. | 604/321 |
| 4,605,400 | 8/1968 | Kurtz et al. | 604/319 |

FOREIGN PATENT DOCUMENTS 1401305  1/1969  Fed. Rep. of Germany ... 137/DIG. 8

Primary Examiner—Alan Cohan
Attorney, Agent, or Firm—Larson and Taylor

[57] ABSTRACT

A regulator is provided for controlling the degree of suction within a collection chamber in a drainage device. The regulator includes a means for measuring the degree of negativity within the chamber and a feedback passageway leading from the measuring means to the suction source. When the measuring means detects a degree of negativity which is equal to or greater than a predetermined value in relation to the available suction the feedback passageway is opened to atmosphere and when the degree of negativity becomes less than the predetermined value the feedback passageway is closed so as to impose the full suction of the suction source upon the chamber.

5 Claims, 3 Drawing Figures

SUCTION REGULATOR

The present application is a continuation-in-part of application Ser. No. 821,530 filed Jan. 24, 1986 which is a continuation-in-part application Ser. No. 667,814, filed Nov. 2, 1984 both now abandoned.

The present invention relates to a device for regulating the suction level applied to a device connected with the body cavity of a patient.

In underwater drainage devices such as disclosed in U.S. Pat. No. 3,363,626 issued Jan. 16, 1968, there is provided means for regulating the suction level to reduce the suction from that available from the wall outlet in a hospital room to a predetermined value such as, for example, −20 to −30 centimeters of water. This means generally comprises a manometer which includes a U tube having a large arm and small arm with the small arm open to atmosphere. The U tube is filled to the level at which suction is desired and when the applied suction is greater than that desired, air will bubble through the U tube from the opening to atmosphere. This device will serve to maintain the suction level applied to the drainage device at the desired value provided there is no substantial air leak within the patient's pleural cavity.

In U.S. Pat. No. 4,605,400 issued Aug. 12, 1986, there is disclosed a drainage device in which the manometer regulator disclosed in U.S. Pat. No. 3,363,626 is replaced with a series of alves which open at predetermined suction levels to maintain the desired degree of negativity within the drainage device.

It obviously is particularly desirable to maintain a predetermined suction level within the pleural cavity when an air leak exists in the pleural cavity so as to maintain the lung in a fully expanded condition. With devices such as described in U.S. Pat. No. 4,605,400 even when the wall suction is as high as −50 centimeters of water and the suction control chamber is set to maintain a suction level of −20 centimeters of water, the actual suction level in the collection chamber may be as low as −12 centimeters of water with a large air leak in the pleural cavity.

The present invention achieves the objective of permitting the full wall suction available to be applied to a drainage device in the event the suction level does not maintain the desired level by providing means for determining the actual degree of suction within the drainage device and immediately applying full wall suction in the event the suction level falls below the desired level. This is the equivalent of a physcan placing his thumb over the outlet to atmosphere of a liquid filled manometer regulator as disclosed in U.S. Pat. No. 3,363,626. Thus, according to the present invention there is provided a bellows having the inner chamber thereof connected with the collection chamber of a drainage device. The exterior of the bellows is connected to atmospheric pressure. A passageway is provided from wall suction, the inner end of this passageway being open and disposed immediately below the lower end of the bellows. In one position of the bellows the lower end of the bellows will close the inner end of the passageway so as to exclude atmospheric air from entering the passageway to wall suction. In a raised position of the bellows the lower end of the bellows permits atmospheric air to enter the passageway to wall suction. Thus, when the degree of negativity within the collection chamber is less than a predetermined value, for example, 20 centimeters of water, the bellows will close the passageway from wall suction to atmosphere so as to permit full wall suction to be applied to the collection chamber until the degree of negativity is greater than 20 centimeters of water. When the degree of negativity within the collection chamber is greater than the preset value, the bellows will rise, opening the passageway from wall suction to atmospheric pressure, thus reducing the degree of negativity within the collection chamber.

An object of the present invention is to provide means for regulating the suction level within a drainage device so as to maintain the desired suction level by immediately applying full wall suction to the collection chamber when the degree of negativity is less than the desired level.

A further object of the present invention is to provide a suction regulator for a drainage device which adjusts the applied suction in accordance with the actual suction level existing within the collection chamber.

Another object of the present invention is to provide a pleural drainage device which will permit the application of full wall suction to the collection chamber and pleural cavity in the event of a large air leak within the pleural cavity.

Figure 2:
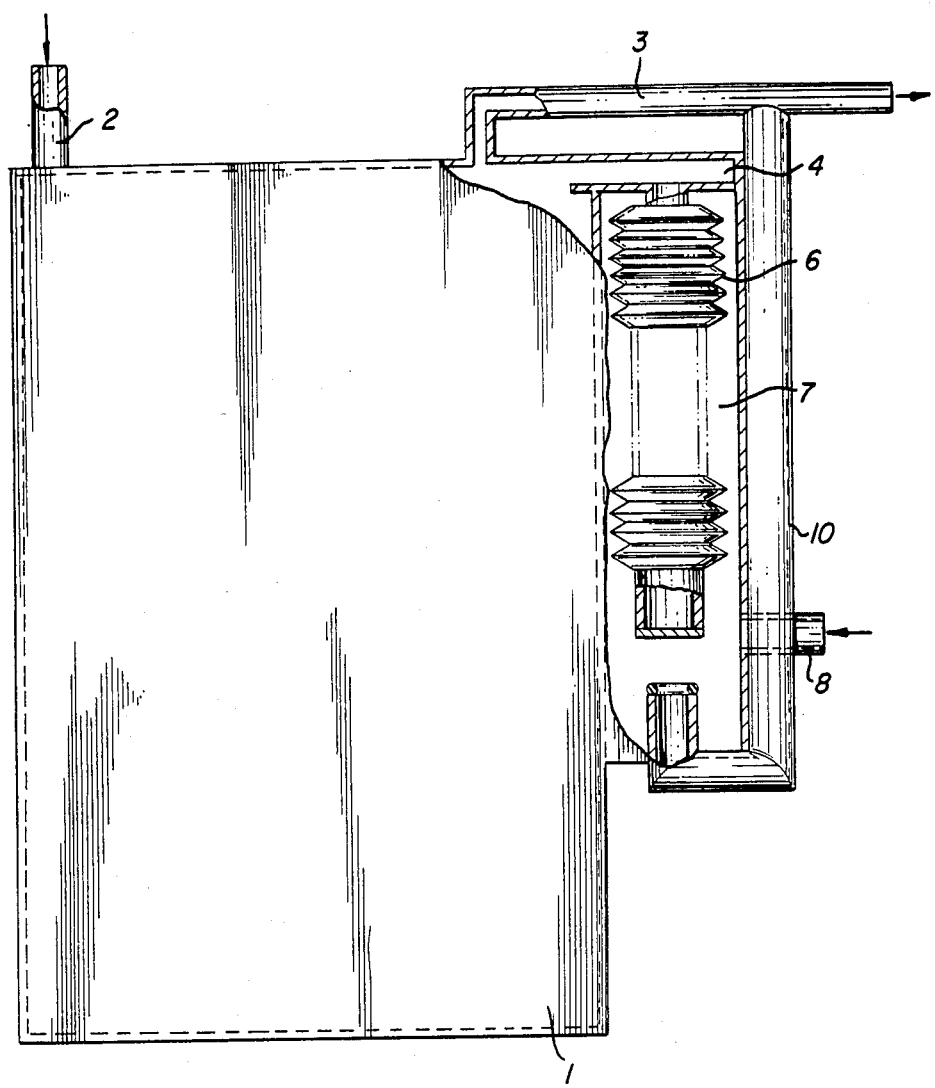
Figure 3:
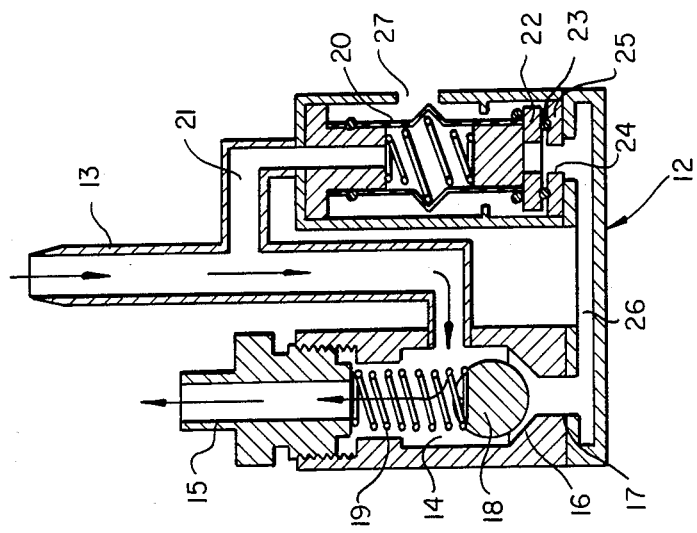

Other objects and many of the attendant advantages of the present invention will become apparent upon consideration of the following detailed specification together with the accompanying drawings wherein:

FIG. 1 is a sectional elevtion of a drainage device showing the suction control valve in a closed position, FIG. 2 is a sectional elevation of the drainage device showing the suction control valve in an open position, and FIG. 3 is a sectional elevation of a suction control system for a drainage device utilizing a ball valve to control the suction level.

Referring to FIG. 1 there is shown at 1 the collection chamber of a drainage device. The details of the drainage device are well known in the prior art and may be as shown in any one of U.S. Pat. Nos. 4,312,351 issued Jan. 26, 1982; 4,296,748 issued Oct. 27, 1981 or 4,396,386 issued Aug. 2, 1983. A connection 2 is provided at the upper end of the drainage device for attachment of a thoracotomy tube. There is further provided a passageway 3 for connecting the collection chamber with a source of suction. The suction source may be the wall suction available in a hospital and means must be provided to reduce the higher suction levels which are normally available from such wall suction sources.

A suction regulator is provided which comprises means for measuring the suction level within the collection chamber together with a feedback passageway for adjusting the suction level of the applied wall suction in relation to the measured suction level existing in the collection chamber.

The measuring means comprises an extended portion 4 of the upper end of the collection chamber having an opening 5 therein for communication with the interior of a bellows 6. In U.S. Pat. No. 4,396,386 issued Aug. 2, 1983, there is disclosed a bellows for measuring the degree of negativity existing in a drainage device. The bellows 6 is disposed within a chamber 7 which is provided with an opening 8 to atmosphere. Thus, the exterior surface of the bellows is exposed to atmospheric pressure. As the degree of negativity within the bellows increases, the bellows will tend to contract, raising the lower end of the bellows.

At the lower end of chamber 7 there is provided the upstanding open end of a passageway 10. The opposite end of passageway 10 connects with passageway 3 which interconnects the collection chamber and wall suction. There is provided an O ring 11 on the open end of passageway 10 to form a seal between the lower end of bellows 6 and the upstanding open end of passageway 10. This seal prevents the entry of atmospheric air into passageway 10 when the lower end of bellows 6 rests on the seal.

In FIG. 2 there is shown the position of the elements of the suction regulator when the negativity within the collection chamber is sufficiently high to cause the bellows to contract. It can be seen that in this condition of the device the passageway 10 is open to atmosphere from outlet 8 and through chamber 7. Thus, atmospheric air enters the passageway 3 and reduces the degree of suction applied to the collection chamber. As the suction level within the collection chamber is reduced, the bellows 6 will be lowered until the passageway 10 is closed to prevent atmospheric air from entering through inlet 8 and the degree of suction applied to the collection chamber is increased.

During normal operation of the device the bellows will be continually rising and falling or "hunting", closing the open end of passageway 10 when the degree of negativity within the collection chamber is less than the desired value and opening the passageway 10 when the full wall suction is applied to increase the degree of negativity within the chamber.

The presently disclosed suction regulator may be observed by the physician as an indicator of the conditions of the patients pleural cavity. Large air leaks within the patient's pleural cavity would tend to lengthen the period during which the passageway 10 is closed and shorten the period during which the passageway 10 is opened.

In FIG. 3 there is shown a suction regulating system utilizing a ball valve and incorporating the present invention. A prior art suction regulating system utilizing ball valves is shown and described in U.S. Pat. No. 4,605,400. However the suction regulating system shown in the aforesaid patent has not effectively maintained the desired degree of negativity within the collection chamber when there is an air leak in the pleural cavity. Tests conducted on such a drainage device simulating a patient air leak produced the following results:

| Air Flow into Wall Suction liters/minute | Wall Suction mm Hg | Patient Air Leak into Collection Chamber liters/minute | Suction Level in Collection Chamber cm $H_2O$ |
|---|---|---|---|
| 28 | 75 | 0 | −21.5 |
| 28 | 75 | 0–2 | −20.5 |
| 28 | 75 | 2–4 | −17.5 |
| 28 | 75 | 4–6 | −14 |
| 28 | 75 | 6–8 | −11 |
| 28 | 75 | 8–10 | −4 |

It can be seen that with patient air leaks of greater than 2 liters per minute the system was unsuccessful in maintaining a desired degree of negativity of −20 cm $H_2O$. With the suction regulator of the present invention the desired degree of negativity can be maintained irrespective of the amount of air leak in the patient's pleural cavity.

In FIG. 3 there is shown a housing 12 which may be integrally formed within a drainage device or attached thereto. A passageway 13 is provided which connects to the collection chamber of the drainage device. This passageway connects within the housing 12 with an internal ball valve chamber 14. The upper end of ball valve chamber 14 opens to passageway 15 connected to a suction source. Thus it can be seen that a passageway is open from the collection chamber of the drainage device through passageway 13, chamber 14 and passageway 15 to a suction source.

The lower end of chamber 14 is formed with a ball valve seat 16 and bore 17. The ball valve 18 and spring normally function to maintain the degree of negativity in the collection chamber at the desired level. This is achieved by admitting atmospheric air through bore 17 and around the ball valve 18. When the degree of negativity within chamber 14 is less than that desired the ball valve 18 will seat on valve seat 16 to close the bore 17 and thus raise the degree of negativity within the chamber 14 and collection chamber.

The suction regulator of the present invention comprises a bellows 20 which has the interior thereof in communication with a passageway 21 connected to the passageway 13 leading to the collection chamber. The lower end 22 of the bellows together with O ring 23 is shown as closing a passageway 24 in valve seat 25. Passageway 24 communicates with a chamber 26 in the lower end of housing 12. Chamber 26 is open to bore 17 in valve seat 16. An opening 27 is provided in the housing surrounding the bellows 20. The opening 27 provides the volume surrounding the bellows with communication with atmosphere.

The bellows is constructed so that when the degree of negativity within the passageways 21 and 13 are at the desired level of negativity or at a greater degree of negativity than the predetermined level the bellows will be drawn upwardly to open passageway 24 to atmosphere. In this position the ball valve 18 will function to maintain the correct level of negativity within the collection chamber. In the event of an air leak within the pleural cavity which is of sufficient degree to cause the level of negativity in the collection chamber to fall below the desired level, the bellows will lower to close passageway 24. This will cause full wall suction to be applied to the collection chamber. Thus, by virtue of the herein disclosed improved suction regulator system assurance is provided that the desired degree of negativity will be maintained in the collection chamber even in the event of a large air leak in the patient's pleural cavity.

Obviously many modifications and variations of the present invention are possible in light of the foregoing teachings.

What is claimed as new and is desired to be secured by Letters Patent is:

1. A suction regulator for regulating the degree of suction in a drainage device having a collection chamber with an opening in the upper end thereof connected to a thoracotomy tube and a passageway connected with a source of suction, valve means disposed between said source of suction and said collection chamber for applying all available suction from the source of suction to the collection chamber in the event the suction level in the collection chamber falls below a desired level, said valve means comprising a bellows, duct means providing communication between the interior of the bellows and the interior of the collection chamber, the exterior of the bellows being in communication with atmospheric air, a feedback passageway having one end thereof connected to the passageway to the suction source downstream of the duct means connection to the collection chamber and the other end of said feedback passageway being positioned to be closed by the lower end of the bellows whereby when the degree of negativity within the collection chamber becomes less than a predetermined value the bellows closes the feedback passageway to prevent atmospheric air from entering the feedback passageway to suction so as to apply all available suction from the suction source directly to the collection chamber and the feedback passageway being open to atmosphere when the suction level in the collection chamber is at the desired or greater value due to no excess of air passing through the thoracotomy tube.

2. A suction regulator according to claim 1 wherein the interface between the end of the bellows and the feedback passageway is visible to a physician to observe movements of the lower end of the bellows.

3. A suction regulator for a drainage device having a collection chamber comprising a first passageway extending from the collection chamber to a source of suction, a parallel second passageway having the ends thereof in communication with said first passageway, an outlet to atmosphere in said second passageway, first valve means disposed in said second passageway for closing the outlet to atmosphere in response to decreased levels of negativity in said first passageway and second valve means disposed in said second passageway downstream of said first valve means for regulating the amount of air admitted to said first passageway when said first valve means opens.

4. A suction regulator according to claim 3 wherein said first valve means comprises a bellows.

5. A suction regulator according to claim 3 wherein said second valve means comprises a ball valve.

* * * * *